(12) United States Patent
Gramage Pina

(10) Patent No.: US 8,016,787 B2
(45) Date of Patent: Sep. 13, 2011

(54) SINGLE-USE SYRINGE

(76) Inventor: Lourdes Gramage Pina, Valencia (ES)

( * ) Notice: Subject to any disclaimer, the term of this patent is extended or adjusted under 35 U.S.C. 154(b) by 0 days.

(21) Appl. No.: 12/518,352

(22) PCT Filed: Jan. 9, 2007

(86) PCT No.: PCT/ES2007/070001
§ 371 (c)(1),
(2), (4) Date: Oct. 28, 2009

(87) PCT Pub. No.: WO2008/084124
PCT Pub. Date: Jul. 17, 2008

(65) Prior Publication Data
US 2010/0049124 A1    Feb. 25, 2010

(51) Int. Cl.
*A61M 5/00* (2006.01)
(52) U.S. Cl. .................. 604/110; 604/208; 604/228
(58) Field of Classification Search .............. 604/110, 604/187, 192, 208, 210, 218, 220, 228
See application file for complete search history.

(56) References Cited

U.S. PATENT DOCUMENTS

| | | | | |
|---|---|---|---|---|
| 4,826,483 A | * | 5/1989 | Molnar, IV | 604/110 |
| 5,019,045 A | * | 5/1991 | Lee | 604/110 |
| 6,287,282 B1 | * | 9/2001 | Bonaldo et al. | 604/198 |
| 6,368,306 B1 | * | 4/2002 | Koska | 604/218 |
| 6,656,165 B2 | * | 12/2003 | Chen | 604/240 |
| 6,972,006 B2 | * | 12/2005 | Ferguson | 604/208 |
| 2004/0176722 A1 | * | 9/2004 | Capes et al. | 604/110 |
| 2004/0186428 A1 | * | 9/2004 | Ray | 604/110 |
| 2005/0070849 A1 | * | 3/2005 | Yang | 604/165.03 |
| 2006/0084913 A1 | * | 4/2006 | Lo | 604/110 |
| 2007/0049868 A1 | * | 3/2007 | Woehr et al. | 604/110 |
| 2008/0249462 A1 | * | 10/2008 | Smith | 604/60 |

FOREIGN PATENT DOCUMENTS

| | | |
|---|---|---|
| DE | 20 2004 017 971 | 3/2005 |
| ES | 1 051 002 | 6/2002 |
| ES | 1 055 675 | 1/2004 |

* cited by examiner

*Primary Examiner* — Nicholas D Lucchesi
*Assistant Examiner* — Gerald Landry, II
(74) *Attorney, Agent, or Firm* — Ladas & Parry LLP

(57) ABSTRACT

Self-disabling or self-locking single-use syringe of the passive type, i.e., one that is self-locked after first use of the syringe, in such a way that any attempted reuse is prevented, and is characterised in that it comprises at least two rings provided on the internal face of the barrel and having the general shape of a circular crown with a variable internal radius, and in that each of the longitudinal fins of the piston has a height which is different from that of at least one of the other fins, in such a way that the plunger can be inserted tightly through the space defined by the variable internal radius of the barrel rings. In this way resistance to the passage of the piston is minimised, thereby reducing the risk of causing bruises, and with a manufacturing cost substantially similar to that of conventional syringes.

16 Claims, 7 Drawing Sheets

SINGLE-USE SYRINGE

FIELD OF THE INVENTION

The present invention relates to a single-use syringe of the self-destructible or passive self-lockable type, namely self-locking thereof occurs after the syringe has been used a first time, independently of the user's will.

PRIOR ART

Syringes are a type of instrument widely used in the medical and health sector in order to administer drugs, insulin, etc., to patients in need thereof. For health safety reasons it is desirable that this type of syringe should be used once only so that diseases or illnesses cannot be passed from one patient to another. However, this is not always the case, especially amongst drug-dependent persons who usually use the syringes again on more than one occasion, with the consequent medical risk which this involves. Such reuse is feasible because in conventional syringes there is nothing to prevent or least discourage reuse thereof. The existence of single-use syringes which self-destruct or self-lock automatically when used a first and only time theoretically solves this problem of preventing reuse of already used syringes. However, it is also desirable that syringes intended for this purpose should have other additional characteristics:

1. Be tamper-proof for those users who attempt to reuse them. Otherwise, a user could interfere with them, deactivating the self-destructing or self-locking systems, with the aim of being able to reuse them indefinitely.
2. Be of the passive type, namely have a design such that total or partial locking and breakage occurs passively, irrespective of the user's will.
3. Be easy to break when disposed of and difficult to break during normal use.
4. Have a low manufacturing cost. In the prior art it is possible to find a large number of documents which describe single-use syringes. However, practically none of them have been successful commercially owing to the fact that sanitary syringes are subject to a further constraint: their cost. Syringes for sanitary use are mainly acquired by the national health authorities in various countries for use in health centres, hospitals, etc. For said national health authorities cost is a factor of prime importance such that a single-use syringe which has a cost much higher than that of the current syringes is unacceptable, even despite its undoubted advantages in terms of health safety. Consequently, in order for a single-use syringe to be successful in the health sector, its manufacturing cost must be substantially the same as that of conventional syringes, or, expressed differently, it must be substantially as easy to manufacture as conventional syringes.

For example, the international publication WO02/22194 in the name of Li describes a self-destructible syringe. However, its design is complex, requiring a large number of internal parts, which increases its manufacturing cost to an unacceptable level.

The international publication WO89/00057 describes a self-lockable syringe whose locking system is based on a series of grooves and tongues arranged inside the plunger and barrel. However, since the locking action occurs only once the plunger has already performed a certain part of its stroke, and not before, this syringe can be easily tampered with by a user who wishes to use it again, by simply extracting the plunger before initial use and cutting the tongues of the barrel using a knife or cutter such as to make the locking system unusable.

Other documents, such as US20040199113, US20040176722 and ES1051002U, describe a syringe which has a weakened part at the end of the plunger, intended to break under pressure when the plunger reaches the end of its stroke. However, a careful user may not manage to break this weakened part so that the syringe would remain locked only if actively desired by the user. Moreover, a user who wishes to cause locking of the syringe when used the first time would have to apply additional pressure to the plunger at the end of its stroke, causing a pressure-induced haematoma in the patient.

Finally, the document ES 1055675U, which is considered to be the most closely related prior art, describes a syringe which is locked by means of tongues on the plunger which engage inside grooves located at the top and bottom ends of the barrel. Owing to the presence of grooves at the top of the barrel which prevent passage of the plunger if an attempt is made to remove it before initial use, tampering with the syringe is impossible. Moreover, locking of the syringe occurs automatically after first use independently of the user's will. However, this syringe, owing to the design of its tongues and grooves, at the time of use requires the user to exert a relatively high additional pressure in order to overcome the resistance offered by the tongues and grooves to passage of the piston and thus inject the liquid into the patient, this being frequently the cause of an undesirable haematoma in the injected zone.

It would be desirable, therefore, to provide a novel syringe which is devoid of the disadvantages of syringes of the prior art and in particular which has characteristics which prevent the syringe from being deformed or do not require the use of excessive pressure which causes a "surge" effect when the liquid is injected, thereby avoiding the formation of haematomas in the patient.

SUMMARY OF THE INVENTION

The problem to be solved by the present invention is that of providing a single-use syringe which overcomes the drawbacks of existing syringes according to the prior art and, more specifically, preventing the formation of haematomas in the patient, while maintaining the characteristics of being self-locking after initial use, difficult to tamper with and simple in terms of design.

The solution consists in the fact that the inventors have created a syringe which maintains the desirable characteristics mentioned—i.e. self-locking after initial use, difficult to tamper with and simple design—by providing a syringe which comprises a barrel which has inside at least two protrusions in the form of rings with a general circular rim shape which have a variable inner radius and triangular or near triangular cross-section and are located respectively at the top and bottom of the barrel on its inner side and a plunger which comprises a plurality of ribs, each of which has a height which is reduced by the amount needed to allow the plunger to be inserted in a close-fitting manner through the space defined by the variable inner-radius of the barrel rings. By means of these characteristics it is possible to provide a syringe with the advantages indicated, avoiding in particular the formation of haematomas in the patient owing to the present design of rings and ribs which minimises the resistance to passage of the plunger, and a manufacturing cost which is substantially similar to that of conventional syringes.

Consequently, a first aspect of the invention relates to a single-use syringe which comprises:
a) a barrel (10) which has an inner surface which defines a chamber for retaining a fluid;

b) a plunger (1) which comprises an elongated body, said elongated body comprising a plurality of longitudinal ribs (2), and c) a piston (3) which is connected to the end of the plunger close to the needle, the outer surface of the piston forming a fluid-tight connection with the inner surface of the barrel, characterised in that:

the barrel comprises at least two rings situated on the inner side of the barrel, at least one being situated on the distal part (8) and at least one being situated on the proximal part (9) of the barrel relative to the needle, said rings having the general shape of a circular rim (see general diagram in FIG. 10) with an outer radius (R) coinciding with the radius of the inner side of the barrel and a variable inner radius (r), and in that each one of the longitudinal ribs (2) of the plunger has a height which is constant along its entire length, but different from that of at least one of the other ribs, said height being suitable on each rib for allowing insertion of the plunger (1) through the space defined by the variable inner radius of the said rings (8, 9) of the barrel in a close-fitting manner.

The two rings mentioned may surround the entire inner perimeter of the barrel (10), although they preferably do not surround it completely, having a general crescent shape which is more or less closed.

Figure 3:
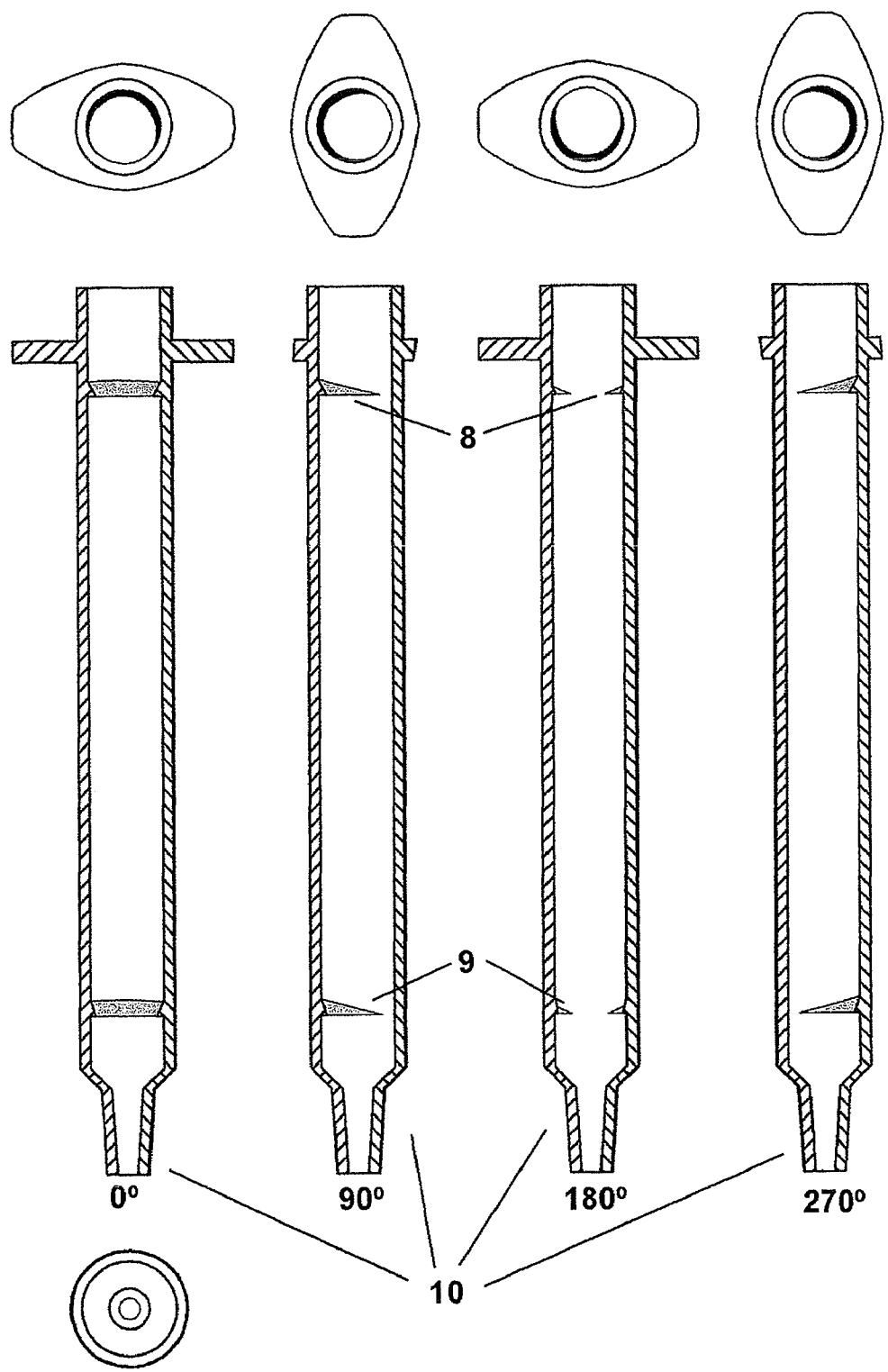
FIG. 3 also shows views, in positions at 90° intervals, of the barrel (10) used in the single-use syringe according to the invention. In said figure it is possible to see the two rings with a substantially triangular cross-section according to the invention situated on the inner top part (8) and inner bottom part (9) of the barrel. In a preferred embodiment of the invention, these rings have a substantially triangular shape, in particular the shape of a right-angled triangle, one of the catheti corresponding to the inner wall of the cylinder, the other cathetus being situated perpendicularly to the inner wall of the barrel in the zone closest to the needle and so that the hypotenuse is forced to be a kind of inclined surface which may be straight or slightly curved so that the plunger slides smoothly during its travel towards the end close to the needle, while once said piston has passed beyond said ring it will be difficult for it to move backwards again.

In a preferred embodiment of the invention, shown in FIG. 3, these rings are incomplete rings which do not completely close the inner circumference of the barrel and which have a variable radius which has a maximum value on one of the sides of the barrel (0° view), intermediate value on the two sides situated at 90° with respect to the first side (90° and 270° views) and minimum or substantially zero value on the side opposite to the first side (180° view).

Figure 4:
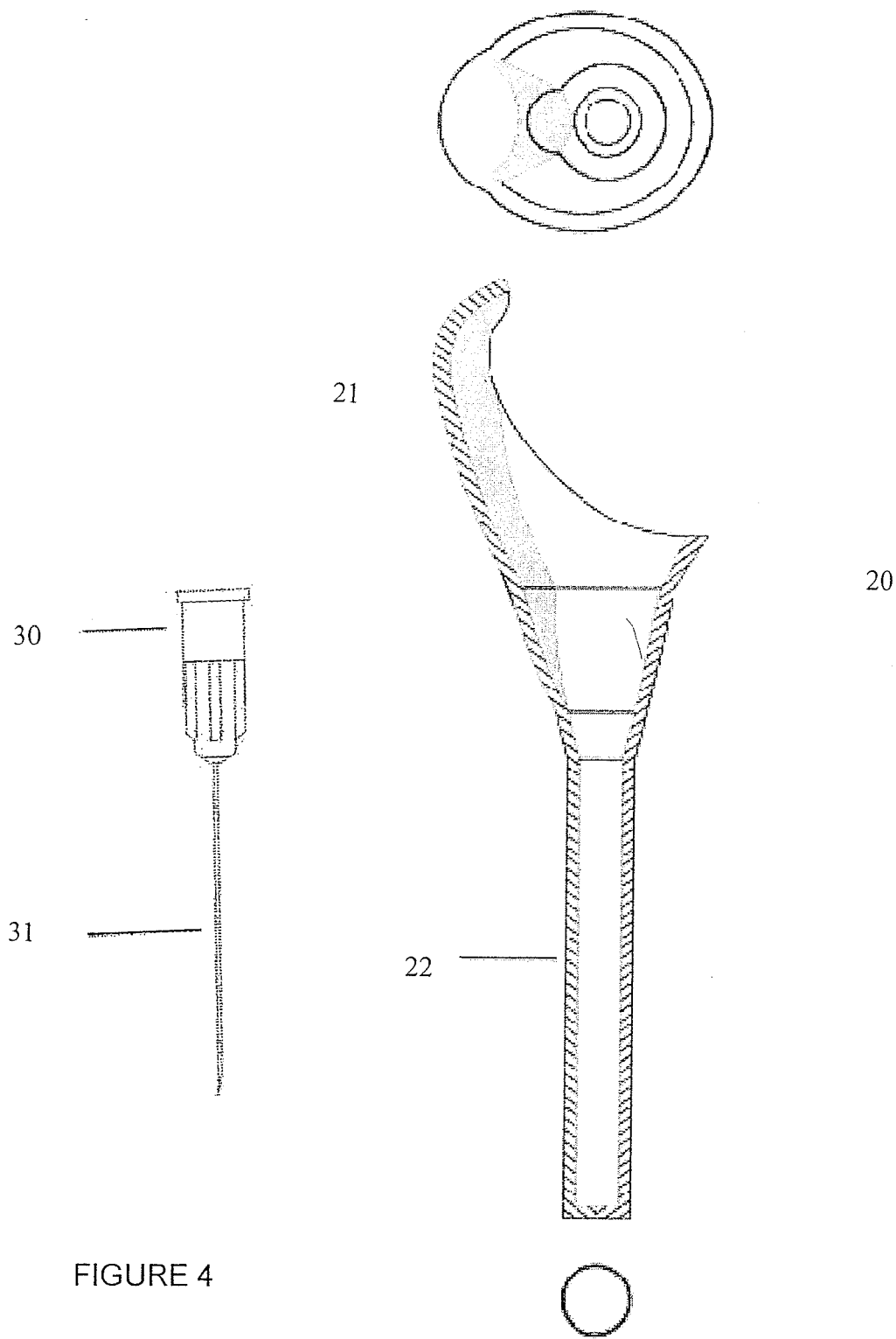

FIG. 4 shows a needle suitable for use in connection with the syringe according to the present invention and having an upper region (30) and a lower region (31).

Figure 5:

FIG. 5 shows an optional cap—present in a preferred embodiment of the invention—which may be used with the single-use syringe according to the invention. This cap has the characteristic feature that it has a substantially conical shape with one side widened so as to facilitate insertion of the needle when not in use. This cap has a substantially conical shape with one side extended in the form of a claw, being in reality a protuberance of the cylinder segment type terminating in a sphere segment such that, upon insertion of the needle, the needle engages inside the cap in a direction perpendicular to the way in which it is then inserted. Namely, instead of inserting the needle in a single direction, as occurs with the caps of the prior art, the user will perform engagement in a direction perpendicular to the shank of the cover and for this reason will never risk being pricked.

Figure 6:
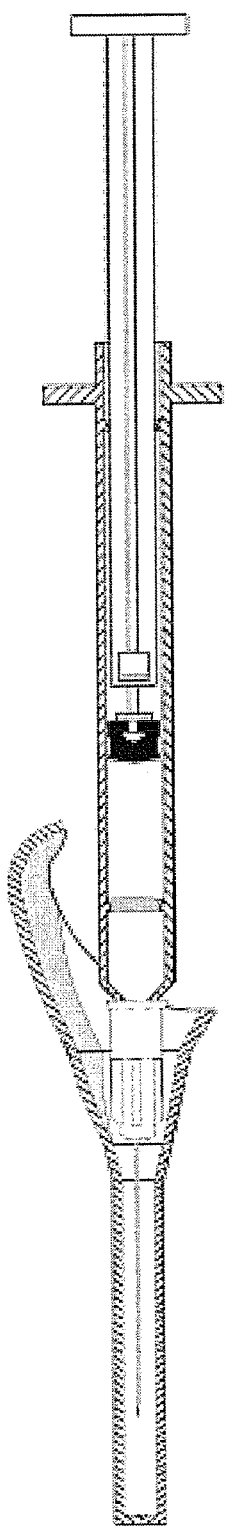
Figure 7:
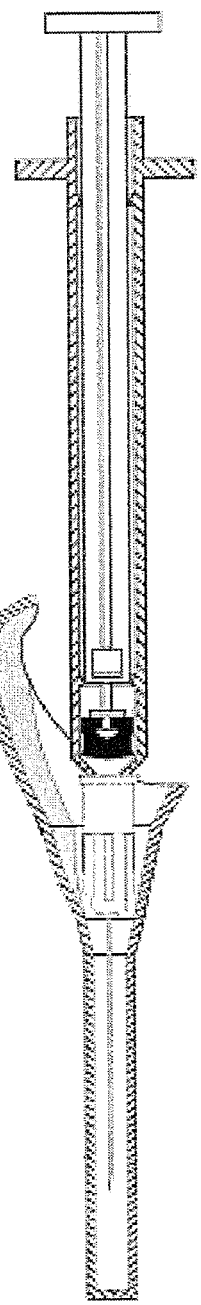
Figure 8:
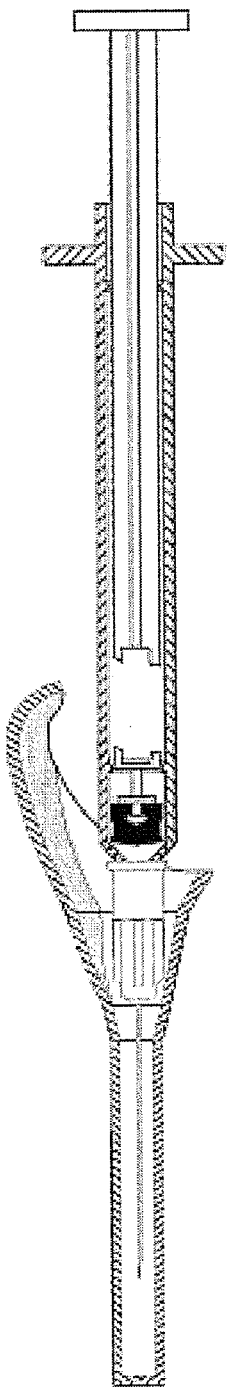

FIGS. 6 to 8 show the syringe assembled and in the operating condition. FIG. 6 shows the position of the plunger when the user is injecting liquid, such that the piston (3) is situated half way along its stroke. In FIG. 7, the plunger has reached the end of its stroke and the piston (3) is locked by the bottom ring. FIG. 8 shows the plunger broken along its weakened part as a result of an attempt to extract it after it has been locked.

Figure 9:
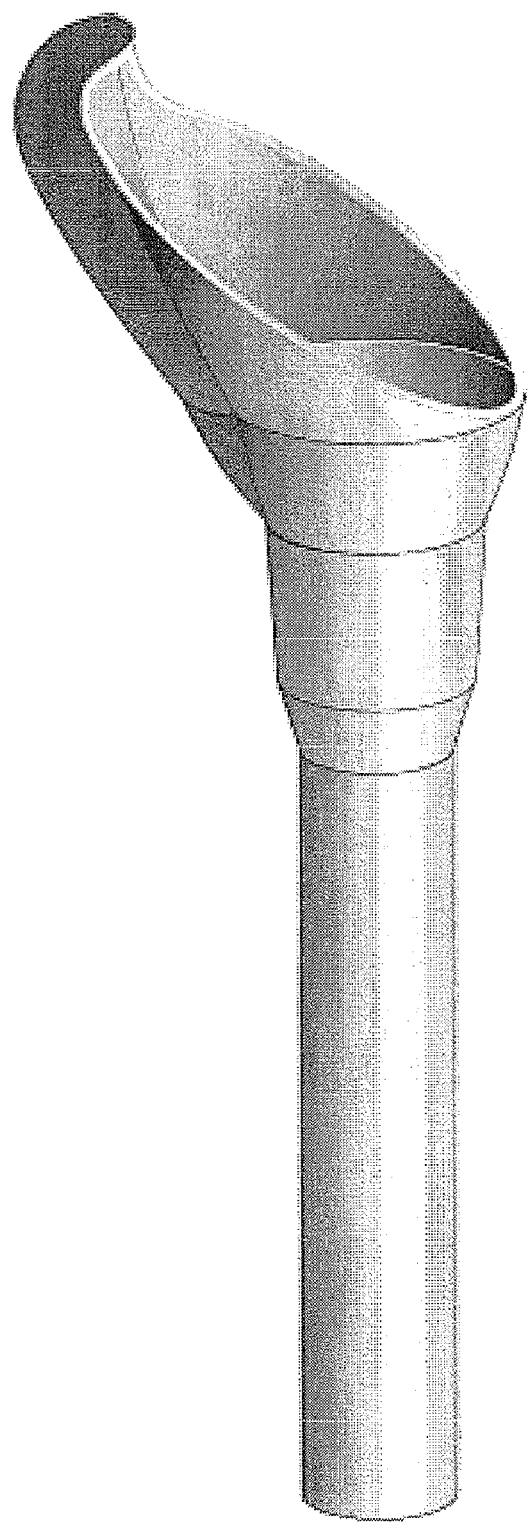

FIG. 9 shows a three-dimensional view of the cap according to FIG. 7.

Figure 10:
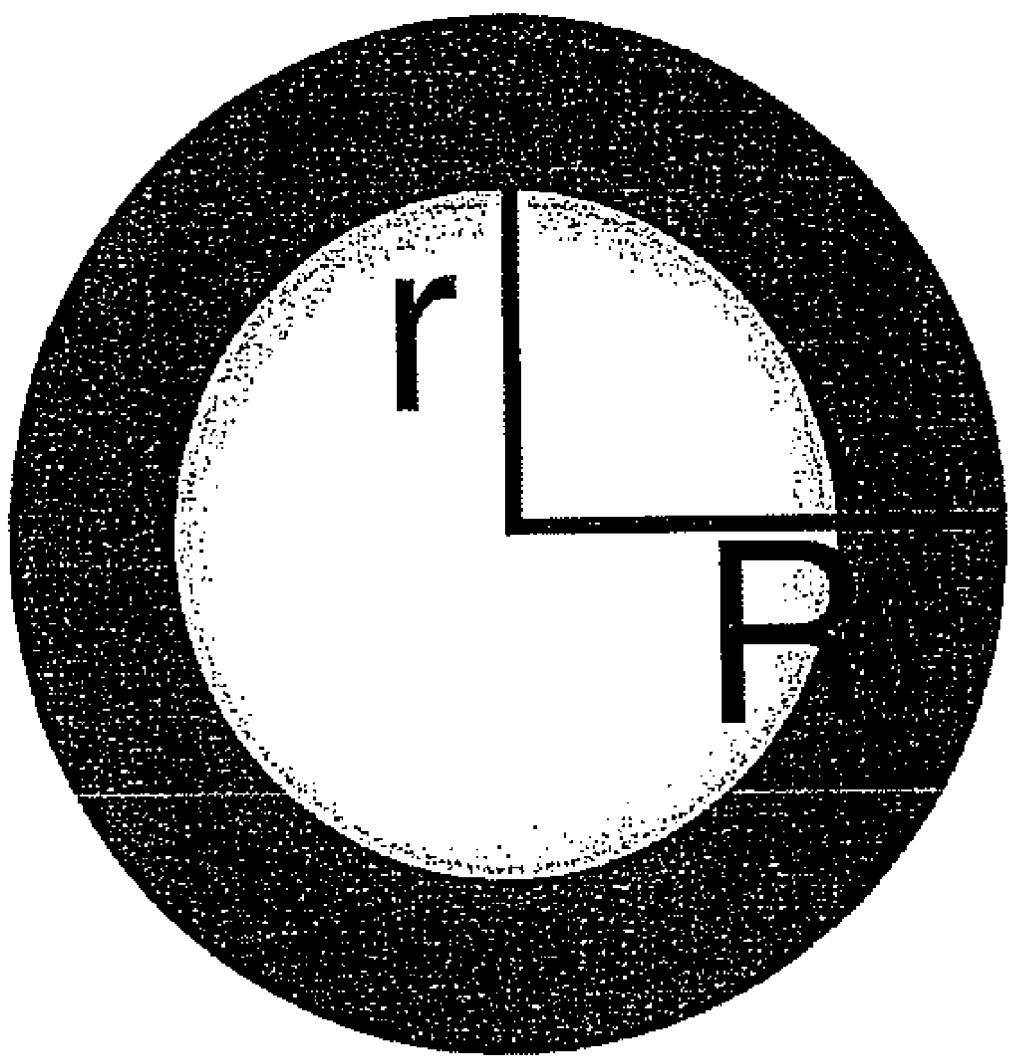

FIG. 10 is a geometrical illustration of a circular rim showing its inner radius (r) and outer radius (R).

DETAILED DESCRIPTION OF THE INVENTION

Below the preferred embodiments of the invention, which are provided solely by way of illustration and do not limit the scope of the invention in any way, are described.

Figure 1:
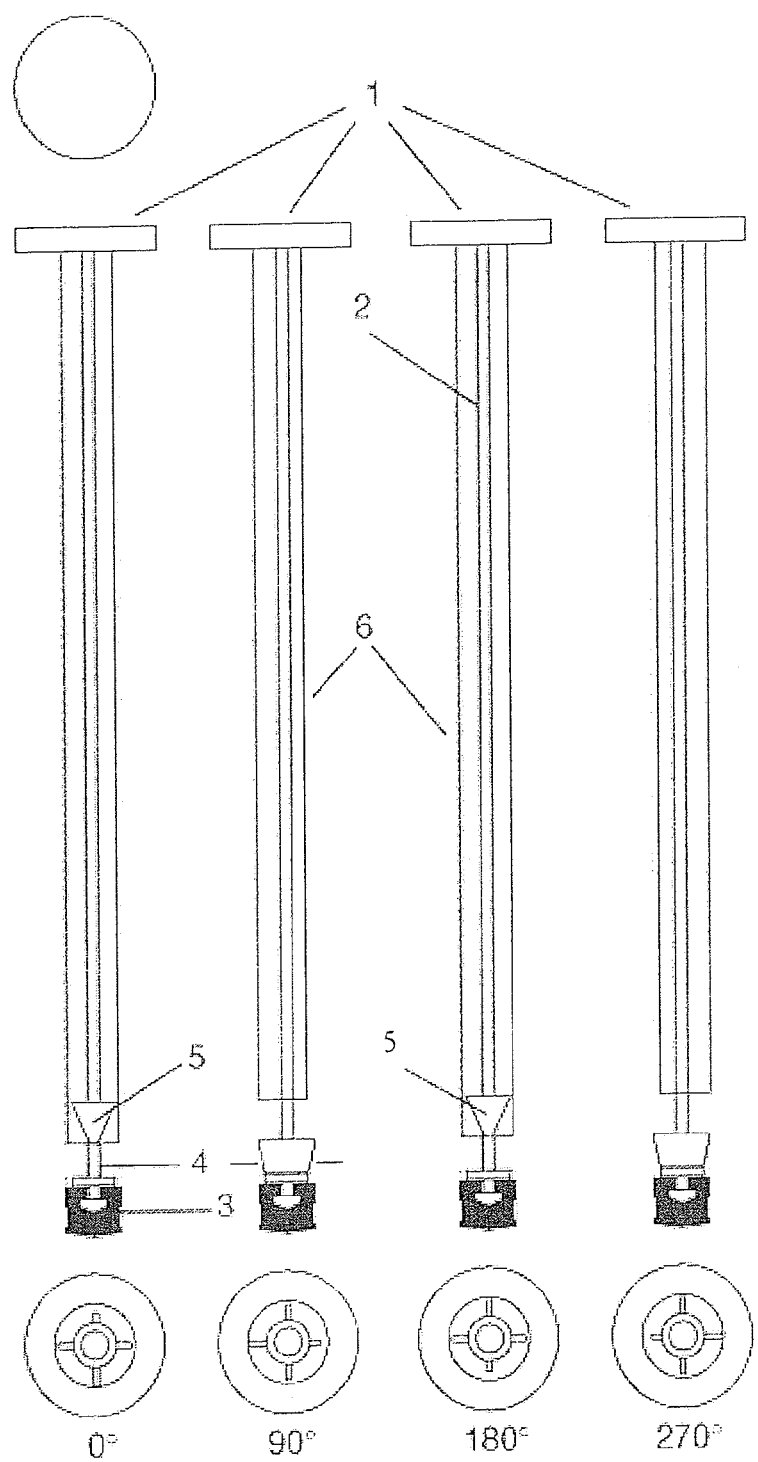
FIG. 1 shows successive views, in positions at 90° intervals, of the plunger used in the single-use syringe according to the present invention. In this figure it can be seen how the plunger (1) comprises a plurality of ribs (2), preferably four in number, which extend longitudinally along the plunger as far as its end part, where the piston (3) is situated, said piston being typically a rubber part, separated from the plunger by a connecting piece (4). The end of the plunger close to the needle has a weakened zone in the form of an orifice which will generally have a variable shape, preferably polygonal shape (5), with the aim of favouring easy breakage thereof at the corners of the polygon. In the embodiment shown in the Figure, said orifice is shown with a triangular shape. Each of the ribs has a different height (broken lines (6)), which height is suitable in each case for allowing insertion of the plunger in a close-fitting manner through the space defined by the barrel rings which have a variable inner radius. Preferably, the length of the plunger ribs will also be different, being longer in those cases where the ribs project towards the needle in such a way as to form the part of the plunger provided with an inner orifice which is preferably polygonal as defined above (see the 0° and 180° views in FIG. 1).

Plunger:

The plunger is shown in detail in FIG. 1. In said figure it can be seen that the plunger comprises:

an elongated body which defines a longitudinal axis, said elongated body comprising a plurality of longitudinal ribs (2) which extend substantially along the entire length of the plunger, and each one of the longitudinal ribs (2) of the plunger has a height which is constant along its entire length, but different from the height of the other ribs, said height being suitable for allowing insertion of the plunger (1) in a close-fitting manner through the space defined by the said variable-radius rings (8, 9) of the barrel, the height of each one of said rings being reduced by the amount necessary for allowing insertion of the plunger in a close-fitting manner through the space defined by the rings of the barrel; the ribs are preferably four in number since this is the number of ribs present in conventional syringes; however, the invention is not limited by the number of ribs and any number of ribs is acceptable, provided that their number and height is variable in such a way that the plunger can be inserted in a close-fitting manner through the space defined by the barrel rings which in turn also have a variable inner radius; the plunger also comprises a weakened zone which is situated preferably at the distal end of the plunger body and which may have any form, being preferably an orifice with a polygonal—generally triangular or square-shape;

a connecting piece (4) which joins the plunger to the piston (3); and a piston (3), usually a rubber part, the outer surface of which forms a fluid-tight connection with the inner surface of the barrel.

Figure 2:
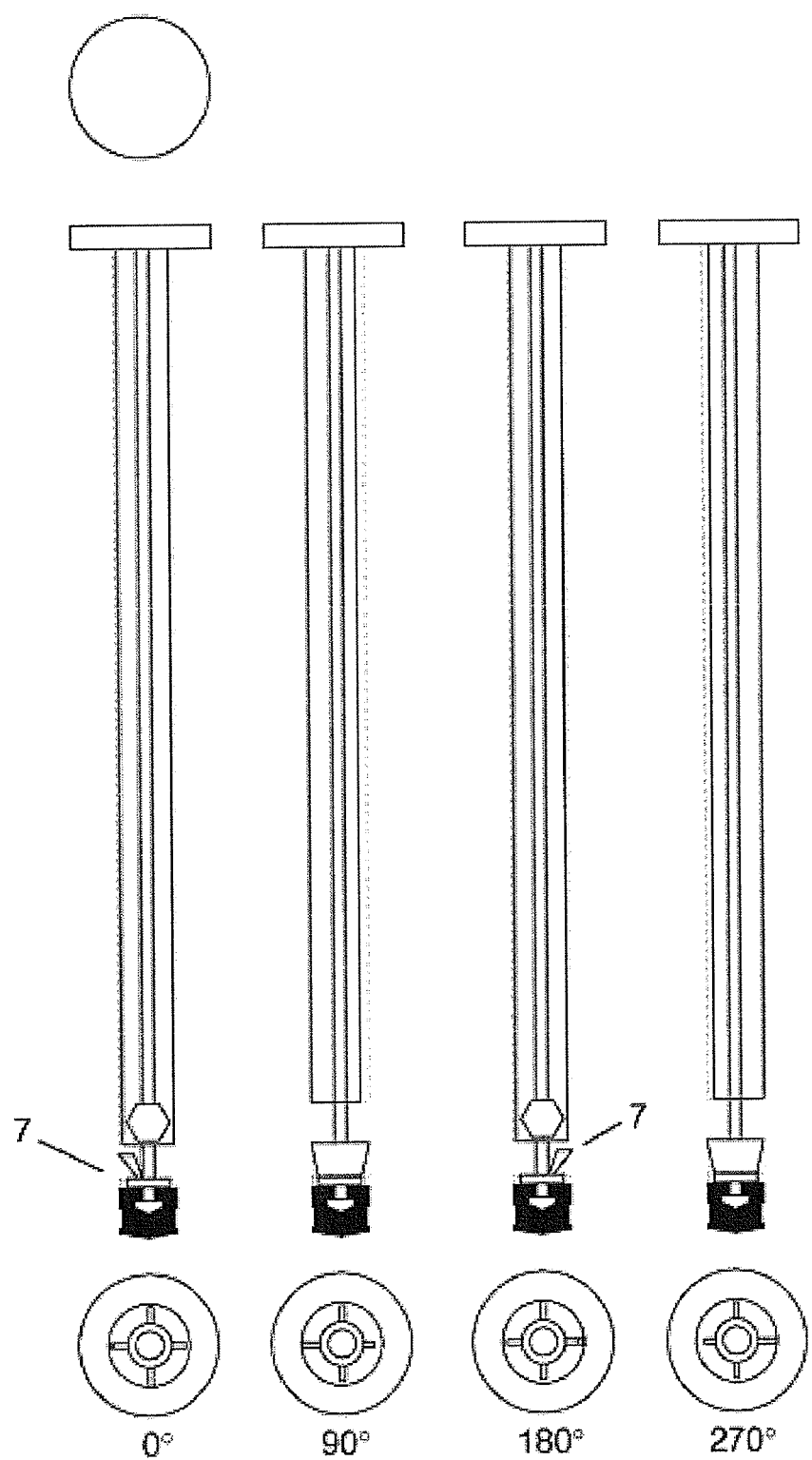
FIG. 2 shows a further embodiment according to the invention which includes an optional tongue (7) which protrudes slightly from the piston so as to increase its locking capacity. In this case also the weakened zone in the form of an orifice situated at the end of the plunger close to the needle has been shown with a hexagonal shape.

FIG. 2 shows an alternative embodiment of the plunger, comprising an additional tongue which projects slightly from the piston so that it increases the capacity for locking the plunger by means of the barrel rings.

Barrel:

The syringe barrel is shown in detail in FIG. 3. This FIG. 3 also shows views, in positions at 90° intervals; of the barrel used in the single-use syringe according to the invention. In said figure it is possible to see the two rings with a substantially triangular cross-section and variable radius situated respectively on the inner top part (8) and inner bottom part (9) of the barrel. Said rings may be completely closed, but preferably they are not closed and have a crescent shape; the rings have a substantially triangular cross-section and the general shape of a circular rim with a variable inner radius so that the outer radius of each ring will always be the inner radius of the barrel, with which it makes integral contact, while the inner radius of each ring will be variable so as to minimise the total surface area of the ring so that it offers the least possible resistance to passage of the plunger, while causing breakage in the case of improper use, so that, preferably, they have a minimum inner radius on one of the sides of the barrel (see 0° view), an intermediate radius on the two sides situated at 90° from the first side (see 90° and 270° views) and an inner radius which has a maximum value or coincides with the outer radius (in which case the thickness will be substantially zero) on the side opposite to the first side (see 180° view). The general shape of the profile or cross-section of the rings is that of a wedge or triangle as explained above so that it is possible to insert the plunger inside the barrel, but not extract it easily.

In an alternative embodiment of the invention, the said rings (8, 9) of the barrel are not continuous, but are formed by more than one section with a discontinuous shape.

The position of the rings on the inner surface of the barrel may vary so that it is possible to determine the volume amount of liquid which can be injected into the user before locking of the plunger occurs. Therefore, although it is normally desirable that the top ring should be situated close to the distal end of the barrel relative to the needle with the aim of maximizing the useful volume, the bottom ring may be situated in a position close to the proximal end of the barrel relative to the needle, being separated from said end close to the needle by a greater or smaller distance, and in all cases preferably within the first third of the length of the barrel with respect to the needle. In this way, if the bottom ring is situated in a position on the barrel further away from the end close to the needle, locking of the plunger will occur when a smaller amount of liquid has been injected into the user. If, on the other hand, the bottom ring is situated in a position closer to the proximal end of the plunger relative to the needle, there is a greater useful volume of liquid which can be injected before locking of the plunger occurs, such that a drug-dependent user could take advantage of this fact in order to use the syringe again repeatedly without reaching the plunger locking position. Preferably, the bottom ring will be situated in a position close to the end of the first third of the length of the barrel, with respect to the end close to the needle.

Cap

The cap of the syringe, which is optional although present in a preferred embodiment of the invention, has a substantially conical shape (20) with a widened side prolonged in the form of a claw (21), being in reality a protuberance of the cylinder segment type terminating in a sphere segment so that, upon insertion of the needle, the needle engages inside the cap in a direction perpendicular to the direction in which it is then inserted. Namely, instead of inserting the needle in a single direction, as occurs with caps of the prior art, the user will perform engagement in a direction which is perpendicular to the shank (22) of the cover and in this way never risks being pricked. Once the user has performed engagement in a substantially horizontal direction, the shape of the claw of the cap prevents the needle from coming out of said cap at the top or on the sides and directs the needle towards the cone situated in the vertical plane downwards where it will be fixed in position, avoiding any risk of pricking one's fingers.

Syringe

The syringe according to the invention comprises a plunger with the characteristics described above, which is inserted in a close-fitting manner inside a barrel having the characteristics also described above. The syringe will be provided with a needle which may be supplied together with the rest of the syringe or separately therefrom. When the plunger is inserted inside the barrel, the plunger must be situated so that the lowest-height rib coincides with the largest-radius side of the rings of the barrel; the rib situated on the opposite side, which will be the rib with the smallest or no reduction in height, will coincide with the side where the rings have a substantially zero radius and the intermediate ribs will have an intermediate size matching the radius corresponding to that of the barrel ring at each respective point. In this way it will be possible to insert the plunger in a close-fitting manner inside the barrel, since the barrel rings are semi-rigid so as to allow the piston to pass through them in the direction towards the end of the barrel close to the needle, but prevent it from passing through in the return direction towards the end distant from the needle. Once inserted, the outer surface of the piston (3) forms a substantially fluid-tight closure with the inner surface of the barrel.

The syringe will be used by the user with the plunger inserted inside the barrel so that the piston has passed through the top ring of the barrel; but not the bottom ring (FIG. 6). In this way, the user will be able to draw the corresponding liquid by introducing the syringe needle into said liquid and extracting the plunger to the height necessary for drawing off the desired quantity of liquid, the stroke of the plunger being limited by the top ring (9) of the barrel.

The procedure for using the syringe will be as follows:

1. Initially the piston is situated between both crescent-shaped rings so that there is an air chamber between the needle and the piston, called "dead space".

2. After introducing the needle into the container with distilled water or similar liquid the plunger is moved in the direction away from the needle, drawing off the liquid which remains inside the barrel, together with an air zone.

3. Said liquid is inserted inside a container with the dry extract, without moving the plunger to the end of its stroke.

4. The mixture is collected again once the dry extract has dissolved in the distilled water.

5. The air is extracted from the inside of the syringe.

6. The needle is inserted in the patient's body and the liquid is injected into the patient's body using the conventional method.

7. When the piston reaches the end of its stroke, it is lightly retained in said position. The syringe and needle are extracted from the patient's body.

8. Once extracted from the patient, the needle is inserted inside its cap and the plunger is pulled lightly so as to cause breakage thereof. Should this not be performed voluntarily and an attempt be made to use the syringe again, upon attempting to draw off the distilled water the plunger will break owing to the action of the crescent-shaped ring which retains the piston.

Similarly, the syringe according to the invention cannot be easily tampered with by the user since, should the user attempt to tamper with it prior to initial use, upon trying to extract the plunger from the barrel, the piston (3) will come up against the top ring (8) of the barrel, preventing extraction thereof and also causing breakage of the plunger by means of the aforementioned weakened part should the user persist in the attempt to extract it.

In this way the invention described provides a syringe which has the advantages mentioned, namely a simple design, ability to self-lock after initial use, guarantee of safety in medical and sanitary terms and capacity to resist tampering prior to use thereof.

The invention claimed is:

1. Single-use syringe comprising:
    a barrel which has an inner surface which defines a chamber for retaining a fluid and an exit end through which said fluid may be expelled;
    a plunger which comprises an elongated body, said elongated body comprising a plurality of longitudinal ribs, and
    a piston which is connected to the end of the plunger close to the exit end of the barrel, the outer surface of the piston forming a fluid-tight connection with the inner surface of the barrel, wherein
    the barrel comprises at least two rings situated on the inner side of the barrel, at least one being situated on the distal part and at least one being situated on the proximal part of the barrel relative to the exit end, said rings having the general shape of a circular rim with an outer radius coinciding with the radius of the inner side of the barrel and a variable inner radius, and
    wherein each one of the longitudinal ribs of the plunger has a height which is constant along its entire length, but different from that of at least one of the other ribs, said height being suitable on each rib for allowing insertion of the plunger through the space defined by the variable inner radius of the said rings of the barrel in a close-fitting manner.

2. Syringe according to claim 1, in which the said rings of the barrel are incomplete crescent-shaped rings.

3. Syringe according to claim 1, in which the said rings of the barrel are not continuous, but are formed by more than one section with a discontinuous shape.

4. Syringe according to claim 1, in which the said rings of the barrel have a generally triangular cross-section in the form of a right-angled triangle, one of the catheti being situated adjacent to the inner wall of the barrel, the second cathetus being situated perpendicularly with respect to said inner wall, and the hypotenuse between both catheti forming a surface inclined in the direction of forward movement of the plunger.

5. Syringe according to claim 4, in which the hypotenuse has a curved shape.

6. Syringe according to claim 1, in which the ribs are four in number and in which one of the ribs has a height smaller than that of the other ribs and makes close-fitting contact with the rings of the barrel at a point where said rings have a minimum inner radius, another of the ribs has a height greater than that of the other ribs and makes close-fitting contact with the rings of the barrel on the side where they have an inner radius which has a maximum value or coincides with the inner radius of the barrel, and the two intermediate ribs have a suitable intermediate height such that each of them makes close-fitting contact with the rings of the barrel.

7. Syringe according to claim 1, in which the top ring is situated close to the distal end of the barrel relative to the exit end.

8. Syringe according to claim 1, in which the bottom ring is situated within the first third of the length of the barrel measured from its exit end.

9. Syringe according to claim 1, in which the said rings of the barrel are semi-rigid so that the piston can pass through them in the direction towards the exit end of the barrel, but cannot pass through them in the return direction towards the end distant from the exit end.

10. Syringe according to claim 1, in which the plunger has at its exit end a weakened connecting piece.

11. Syringe according to claim 10, in which the weakened connecting piece comprises at least one orifice situated in the end of the plunger close to the needle.

12. Syringe according to claim 11, in which at least one orifice has a polygonal shape.

13. Syringe according to claim 1, in which the piston comprises additionally a tongue for increasing the locking action of the piston against the rings of the barrel when an attempt is made to extract the plunger once it has been locked.

14. Syringe according to claim 1, which also comprises a needle which forms a fluid connection with the chamber defined by the inner surface of the barrel.

15. Syringe according to claim 14, which also comprises a cap for retaining the needle.

16. Syringe according to claim 15, in which the cap has a substantially conical shape with one side prolonged in the form of a cylinder segment terminating in a claw-shaped sphere segment.

\* \* \* \* \*